(12) United States Patent
Ferree

(10) Patent No.: US 6,755,863 B2
(45) Date of Patent: Jun. 29, 2004

(54) ROTATOR CUFF REPAIR USING ENGINEERED TISSUES

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 250 days.

(21) Appl. No.: 10/171,283

(22) Filed: Jun. 13, 2002

(65) Prior Publication Data

US 2004/0093092 A1 May 13, 2004

Related U.S. Application Data

(63) Continuation-in-part of application No. 09/688,716, filed on Oct. 16, 2000, now Pat. No. 6,454,804, and a continuation-in-part of application No. 09/415,382, filed on Oct. 8, 1999, now Pat. No. 6,419,704.
(60) Provisional application No. 60/159,488, filed on Oct. 14, 1999.

(51) Int. Cl.[7] ................................................. A61F 2/08
(52) U.S. Cl. ............................... 623/19.11; 623/13.17; 623/901; 623/915
(58) Field of Search .......................... 623/13.17, 19.11, 623/908, 915, 919, 17.11

(56) References Cited

U.S. PATENT DOCUMENTS

| | | | |
|---|---|---|---|
| 2,677,369 A | 5/1954 | Knowles | 128/92 |
| 3,366,975 A | 2/1968 | Pangman | 3/36 |
| 3,426,364 A | 2/1969 | Lumb | 3/1 |
| 3,551,560 A | 12/1970 | Thiele | 424/95 |
| 3,593,342 A | 7/1971 | Niebauer | 3/1 |
| 3,648,294 A | 3/1972 | Shahrestani | 3/1 |
| 3,855,638 A | 12/1974 | Pilliar | 3/1 |
| 3,867,728 A | 2/1975 | Substad et al. | 3/1 |
| 3,875,595 A | 4/1975 | Froning | 3/1 |
| 3,883,902 A | 5/1975 | Lynch | 3/36 |
| 4,229,839 A | 10/1980 | Schwemmer | 3/1.91 |
| 4,309,777 A | 1/1982 | Patil | 3/1.91 |
| 4,349,921 A | 9/1982 | Kuntz | 3/1 |
| 4,663,358 A | 5/1987 | Hyon et al. | 521/64 |
| 4,707,872 A | 11/1987 | Hessel | 5/451 |
| 4,714,469 A | 12/1987 | Kenna | 623/17 |
| 4,759,766 A | 7/1988 | Buettner-Janz et al. | 623/17 |
| 4,772,287 A | 9/1988 | Ray et al. | 623/17 |
| 4,801,299 A | 1/1989 | Brendel et al. | 623/16.11 |
| 4,863,477 A | 9/1989 | Monson | 623/17 |
| 4,874,389 A | 10/1989 | Downey | 623/17 |
| 4,904,260 A | 2/1990 | Ray et al. | 623/17 |
| 4,911,718 A | 3/1990 | Lee et al. | 623/17 |
| 4,917,704 A | 4/1990 | Frey et al. | 623/17 |
| 4,932,969 A | 6/1990 | Frey et al. | 623/17 |
| 4,946,378 A | 8/1990 | Hirayama et al. | 623/17 |
| 5,002,576 A | 3/1991 | Fuhrmann et al. | 623/17 |
| 5,035,716 A | 7/1991 | Downey | 623/17 |
| 5,047,055 A | 9/1991 | Bao et al. | 623/17 |
| 5,071,437 A | 12/1991 | Steffee, Arthur D. | 623/17 |
| 5,108,438 A | 4/1992 | Stone | 623/17 |
| 5,123,926 A | 6/1992 | Pisharodi | 623/17 |
| 5,171,280 A | 12/1992 | Baumgartner | 623/17 |
| 5,171,281 A | 12/1992 | Parsons et al. | 623/17 |
| 5,192,326 A | 3/1993 | Bao et al. | 623/17 |
| 5,246,458 A | 9/1993 | Graham | 623/17 |
| 5,258,031 A | 11/1993 | Salib et al. | 623/17 |
| 5,258,043 A | 11/1993 | Stone | 623/66 |
| 5,314,477 A | 5/1994 | Marnay | 623/17 |
| 5,320,644 A | 6/1994 | Baumgartner | 623/17 |
| 5,370,697 A | 12/1994 | Baumgartner | 623/17 |
| 5,375,823 A | 12/1994 | Navas | 267/195 |
| 5,401,269 A | 3/1995 | Buttner-Janz et al. | 623/17 |
| 5,425,773 A | 6/1995 | Boyd et al. | 623/17 |
| 5,441,508 A * | 8/1995 | Gazielly et al. | 606/151 |
| 5,458,642 A | 10/1995 | Beer et al. | 623/17 |
| 5,464,439 A | 11/1995 | Gendler | 623/16.11 |
| 5,514,180 A | 5/1996 | Heggeness et al. | 623/17.11 |
| 5,534,028 A | 7/1996 | Bao et al. | 623/17 |
| 5,534,030 A | 7/1996 | Navarro et al. | 623/17 |
| 5,545,229 A | 8/1996 | Parsons et al. | 623/17.11 |
| 5,556,431 A | 9/1996 | Buttner-Janz | 623/17 |

(List continued on next page.)

OTHER PUBLICATIONS

North American Spine Society 13 Annual Meeting, San Francisco Hilton and Towers. Oct. 28–31, 1998; Barron Lonner Md., Et. al., "Tissue Engineered Regeneration of the Intervertebral Disc".

Orthopedics Today, Jul. 2000.

"Proceedings 14th Annual Meeting" North American Spine Society, Oct. 1999.

"Proceedings 13th annual Meeting" North American Spine Society, Oct. 1998.

Steven Frick MD, Spine vol. 19, No. 16, pp. 1826–1835, 1994.

*Primary Examiner*—Suzette J. Jackson
(74) *Attorney, Agent, or Firm*—Gifford, Krass, Groh, Sprinkle, Anderson & Citkowski, PC

(57) ABSTRACT

Living fibrocytes are combined with rotator cuff extracellular matrix obtained from recently deceased human or animal donors to eliminate pain in patients with tendonitis and other rotator cuff deficiencies. According to the method, fibrocytes from a living donor, preferably the patient, and rotator cuff tissue is harvested from a recently deceased human or animal donor in a manner which retains the extracellular matrix. The harvested cells are combined with the extracellular matrix to produce an engineered rotator cuff tissue, which is then transplanted into or onto a patient's rotator cuff to be repaired. Additional therapeutic substances such as culture medium, growth factors, differentiation factors, hydrogels, polymers, antibiotics, anti-inflammatory medications, or immunosuppressive medications could be added to the transplanted annulus fibrosis tissue. In like fashion, the processes described herein may be used to repair or replace other tissues or organs of the body such as the pancreas, liver, kidney, heart, etc. Healthy live cells would be obtained thorough biopsy and tissue culture. The live cells would be added to the extracellular matrix of tissues or organs harvested to recently deceased human or animals.

8 Claims, No Drawings

U.S. PATENT DOCUMENTS

| | | | |
|---|---|---|---|
| 5,609,635 A | 3/1997 | Michelson | 623/17 |
| 5,645,596 A | 7/1997 | Kim et al. | 623/17 |
| 5,645,597 A | 7/1997 | Krapiva | 623/17 |
| 5,674,294 A | 10/1997 | Bainville et al. | 623/17 |
| 5,674,296 A | 10/1997 | Bryan et al. | 623/17 |
| 5,683,465 A | 11/1997 | Shinn et al. | 623/17 |
| 5,702,450 A | 12/1997 | Bisserie | 623/17 |
| 5,711,960 A | 1/1998 | Shikinami | 424/426 |
| 5,716,416 A | 2/1998 | Lin | 623/17 |
| 5,800,549 A | 9/1998 | Bao et al. | 623/17 |
| 5,824,093 A | 10/1998 | Ray et al. | 623/17 |
| 5,824,094 A | 10/1998 | Serhan et al. | 623/17 |
| 5,865,845 A | 2/1999 | Thalgott | 623/17 |
| 5,865,846 A | 2/1999 | Bryan et al. | 623/17 |
| 5,888,226 A | 3/1999 | Rogozinski | 623/17 |
| 5,893,889 A | 4/1999 | Harrington | 623/17 |
| 5,899,941 A | 5/1999 | Nishijima et al. | 623/17 |
| 5,928,284 A | 7/1999 | Mehdizadeh | 623/17 |
| 5,964,807 A | 10/1999 | Gan et al. | 623/17.11 |
| 5,976,186 A | 11/1999 | Bao et al. | 623/17.16 |
| 6,022,376 A | 2/2000 | Assell et al. | 623/17.16 |
| 6,090,112 A | 7/2000 | Zucherman et al. | 606/61 |
| 6,110,210 A | 8/2000 | Norton et al. | 623/17.16 |
| 6,113,639 A | 9/2000 | Ray et al. | 623/17.16 |
| 6,132,465 A | 10/2000 | Ray et al. | 623/17.16 |
| 6,146,420 A | 11/2000 | McKay | 623/17.11 |
| 6,187,048 B1 | 2/2001 | Milner et al. | 623/17.12 |
| 6,231,615 B1 | 5/2001 | Preissman | 623/23.73 |
| 6,245,107 B1 | 6/2001 | Ferree | 623/17.11 |
| 6,332,779 B1 | 12/2001 | Boyce et al. | 433/215 |
| 6,340,369 B1 | 1/2002 | Ferree | 623/17.11 |
| 2001/0024823 A1 * | 9/2001 | Vukicevic et al. | 435/325 |
| 2003/0100108 A1 * | 5/2003 | Altaman et al. | 435/395 |
| 2003/0144197 A1 * | 7/2003 | Zheng et al. | 514/12 |
| 2003/0212456 A1 * | 11/2003 | Lipchitz et al. | 623/13.17 |
| 2003/0215426 A1 * | 11/2003 | French et al. | 424/93.7 |
| 2003/0228292 A1 * | 12/2003 | Gazit et al. | 424/93.21 |
| 2004/0062753 A1 * | 4/2004 | Rezania et al. | 424/93.7 |
| 2004/0064192 A1 * | 4/2004 | Bubb | 623/23.5 |

* cited by examiner

ROTATOR CUFF REPAIR USING ENGINEERED TISSUES

REFERENCE TO RELATED APPLICATIONS

This application is a continuation-in-part of U.S. patent application Ser. No. 09/688,716, filed Oct. 16, 2000, now U.S. Pat. No. 6,454,804 which claims priority from U.S. provisional patent application Serial No. 60/159,488, filed Oct. 14, 1999; and is also a continuation-in-part of U.S. patent application Ser. No. 09/415,382, filed Oct. 8, 1999. Now U.S. Pat. No. 6,419,704 The entire content of each application is incorporated herein by reference.

FIELD OF THE INVENTION

This invention relates generally to rotator cuff repair, and more particularly, to the use of engineered tissues in conjunction with such treatment.

BACKGROUND OF THE INVENTION

Intervertebral discs provide mobility and a cushion between the vertebrae. At the center of the disc is the nucleus pulposus. The nucleus pulposus is surrounded by the annulus fibrosis, which is comprised of cells (fibrocyte-like and chondrocyte-like), collagen fibers, and non-fibrillar extracellular matrix. The components of the annulus are arranged in 15–25 lamellae around the nucleus pulposus. The fibers in the lamellae alternate their direction of orientation by 30 degrees between each band.

The annulus fibrosis has three important functions. First, the annulus contains the nucleus pulposus. Second, the annulus fibrosis, with other ligaments, connects the vertebrae of the spine. Lastly, the annulus fibrosis helps to control movement between the vertebrae.

The fibers of the annulus can tear causing pain and possible extrusion of the nucleus pulposus. Extrusion of the nucleus pulposus is known as a disc herniation. Disc herniations can compress nerves or the spinal cord resulting in arm or leg pain and dysfunction. Surgery to repair disc herniations leaves a hole in the annulus fibrosis. The hole in the annulus acts as a pathway for additional material to protrude into a nerve, resulting in a recurrence of the herniation.

To date, the treatment of tears or defects of the annulus fibrosis has relied for the most part on eliminating the defective disc or disc function. This may be accomplished by fusing the vertebra on either side of the disc. In terms of replacement, prior-art techniques replace either the nucleus or the nucleus and annulus functions. My co-pending U.S. patent application Ser. No. 09/322,516, and Patent Cooperation Treaty Application Serial No. PCT/US/14708 describe methods and devices to occlude annular defects.

SUMMARY OF THE INVENTION

Certain of my co-pending patent applications and issued patents referenced above disclose the repair of tissues and organs by adding live cells to the extracellular matrix of tissues or organs harvested to recently deceased human or animals. For example, with respect to intervertebral disc repair, fibrocytes, annulus fibrosis cells, cells that differentiate into annulus fibrosis cells, or cells that function like annulus fibrosis cells are harvested and combined with the extracellular matrix of the annulus fibrosis from a recently deceased human or animal to produce an engineered annulus fibrosis.

This previously disclosed invention is not limited to treatment of the intervertebral disc. For example, the invention could also be used to treat other tissues of the body such as the meniscus of the knee. In like fashion, the processes described herein may be used to repair or replace other tissues or organs of the body such as the pancreas, liver, kidney, heart, etc. Healthy live cells would be obtained thorough biopsy and tissue culture. The live cells would be added to the extracellular matrix of tissues or organs harvested to recently deceased human or animals.

According to this invention, living cells are combined with rotator cuff extracellular matrix obtained from recently deceased human or animal donors to create engineered rotator cuff tissue. In the preferred embodiment, fibrocytes from a living donor, preferably the patient, and rotator cuff tissue is harvested from a recently deceased human or animal donor in a manner which retains the extracellular matrix. Precursor or developed rotator cuff cells, chondrocytes, or other living cells that could function like rotator cells or that could differentiate into cells to build a functional rotator cuff may also be used. The harvested cells are combined with the extracellular matrix to produce an engineered rotator cuff tissue, which is then transplanted into or onto a patient's rotator cuff to be repaired.

Additional therapeutic substances such as culture medium, growth factors, differentiation factors, hydrogels, polymers, antibiotics, anti-inflammatory medications, or immunosuppressive medications could be added to the transplanted annulus fibrosis tissue. In like fashion, the processes described herein may be used to repair or replace other tissues or organs of the body such as the pancreas, liver, kidney, heart, etc. Healthy live cells would be obtained thorough biopsy and tissue culture. The live cells would be added to the extracellular matrix of tissues or organs harvested to recently deceased human or animals.

The cells or engineered tissues may be introduced using any surgical technique, including percutaneous or laparoscopic approaches. As one delivery mechanism, a passageway may be formed through the shoulder, with the cells or engineered rotator cuff tissue being introduced through the passageway. In particular, the engineered tissue may be sewn or otherwise adhered to the inside or outside of the existing annulus rotator cuff using standard surgical procedures.

DETAILED DESCRIPTION OF THE INVENTION

Broadly according to the invention, fibrocytes are harvested, cultured, added to annulus fibrosis extracellular matrix material, then sewn or otherwise placed relative to an injured or diseased disc. The annulus fibrosis cells and extracellular matrix are preferably harvested from a live human, though recently deceased human or animal donors may alternatively be used. Depending upon the extent of the harvest, the recipient may function at least in part as a donor, or the tissues from others, including fetal or embryo sources, may be used, preferably having a familial relationship to minimize or avoid the need for immunosuppressive substances. Guidelines for tissue procurement including surgical technique of removal, number of hours between death of the donor and tissue procurement, and testing of the donor for infectious disease, are well described.

Following annulus fibrosis harvest, the tissue is processed to kill the living cells. Care is taken to preserve the extracellular matrix. Guidelines for processing the harvested annulus fibrosis as described are well known to those skilled in the art. For example, the tissue could be frozen and thawed.

Fibrocytes are obtained from a tendon of the patient. For example, a palmaris longus tendon could be removed from one arm of the patient. The harvested fibrocytes are isolated and cultured using standard techniques. The harvested sterile tendon is morselized and washed with phosphate buffered saline. The cells are released from the extracellular matrix with 0.2% clostridial collagenase (Worthington CLS II, 140 u/mg) and agitated. See Klagsburn, "Methods in Enzvmology, Vol. VII. The resulting suspension is filtered with 153.mu.g.nylon sieve (Tetko, Elmford, N.Y.).

The filtered solution is then centrifuged at 1800 rpm to remove the cells. The supernatant above the cells is removed with a micropipette until the cell concentration reaches 5.times.10.sup7 cells/cc. The harvested cells are grown in Hamm's F-12 culture media, 10% fetal calf serum, L-glutamine (292.mu.g/cc), penicillin (100 u/cc), streptomycin (100.mu.g/cc), and asorbic acid (5.mu.g/cc) at 37° C. The above method is described in U.S. Pat. No. 6,060,053, which is incorporated in its entirety herein by reference.

Precursor cells of the annulus fibrosis, annulus fibrosis cells, chondrocytes, or other living cells that could function like annulus fibrosis cells or that could differentiate into cells to build a functional annulus fibrosis may also be used.

The living cells from cell culture are implanted into the donor extracellular matrix to form a living annulus fibrosis. In the preferred embodiment, the cells are injected into small holes drilled into the donor extracellular matrix.

The living cells and extracellular matrix may be added to the patient's disc immediately after combination or after a period of time to allow attachment of the cells to the matrix. Naturally, in the delayed embodiment, the cells would preferably be supported with culture media.

The engineered annulus is added to the inside or the outside of a patient's annulus. Surgical procedures to access the inner or outer surface of the annulus fibrosis are well known to those skilled in the art. The engineered annulus could be sutured, placed against, or "glued" to the patient's annulus. Platelet rich plasma combined with calcium and thrombin or "fibrin glue" could be used to glue the annular tissues together.

Additional therapeutic substances could be added to the transplanted annulus. For example, resorbable culture medium, tissue growth or differentiation factors (recombinant generated morphogenetic proteins, PDGF, TGF-β, EGF/TGF-α, IGF-I, βFGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. may be used.

In an alternative embodiment, living cells are not added to the harvested annulus fibrosis. The harvested annulus fibrosis is processed as described above to kill the living host annulus cells.

Although annulus fibrosis augmentation and/or transplantation is being described herein in detail, the invention is not limited to treatment of the intervertebral disc. For example, the invention could also be used to treat other tissues of the body such as the meniscus of the knee and rotator cuff repair. With respect to the former, a meniscus would be removed from recently deceased humans. The harvested meniscus would be processed to kill the cells but preserve the extracellular matrix. Fibroctyes harvested as described above would then be added to the extracellular matrix prior to insertion of the engineered meniscus into a patient's knee. Similarly, chondrocytes could be harvested and added to the meniscus extracellular matrix as described in my U.S. patent application Ser. Nos. 09/639,309, 09/628,727, 09/638,726, and 09/638,242.

With regard to methods and apparatus associated with engineered rotator cuff tissue, the harvested fibrocytes are added to rotator cuff tissue removed from a recently deceased human. Precursor or developed rotator cuff cells, chondrocytes, or other living cells that could function like rotator cells or that could differentiate into cells to build a functional rotator cuff may also be used. The harvested cellular tissue could be processed to kill the cells but preserve the extracellular matrix. Killing the cells of the allograft rotator cuff tissue minimizes the risk of disease transmission and graft rejection.

Fibrocytes would be added to the harvested rotator cuff tissue extracellular matrix prior to insertion of the engineered rotator cuff into a patient's shoulder. Alternatively, the cells could be added to the harvested rotator cuff during or after the rotator cuff is placed into a patient's shoulder.

In like fashion, the processes described herein may be used to repair or replace other tissues or organs of the body such as the pancreas, liver, kidney, heart, etc. Healthy live cells would be obtained thorough biopsy and tissue culture. The live cells would be added to the extracellular matrix of tissues or organs harvested to recently deceased human or animals.

I claim:

1. A method of rotator cuff repair, comprising the steps of:

harvesting fibrocytes from a living donor;

harvesting rotator cuff tissue from a recently deceased human or animal donor, keeping the extracellular matrix intact;

combining the harvested fibrocytes with the extracellular matrix to produce engineered rotator cuff tissue; and transplanting the engineered rotator cuff tissue into or onto a patient's rotator cuff to be repaired.

2. The method of claim 1, further including the step of delivering the engineered rotator cuff tissue through a percutaneous or laparoscopic procedure.

3. The method of claim 1, further including the step of adding one or more therapeutic substances to the engineered rotator cuff tissue.

4. The method of claim 3, wherein the therapeutic substances include one or more of the following:

culture media, growth factors, differentiation factors, hydrogels, polymers, antibiotics, anti-inflammatory medications, or immunosuppressive medications.

5. The method of claim 1, further including the step of keeping the harvested fibrocytes viable until delivered.

6. An engineered rotator cuff according to the method of claim 1.

7. The engineered rotator cuff of claim 1, further including one or more therapeutic substances.

8. The engineered annulus fibrosis of claim 7, wherein the therapeutic substances include one or more of the following:

culture media, growth factors, differentiation factors, hydrogels, polymers, antibiotics, anti-inflammatory medications, or immunosuppressive medications.

* * * * *